United States Patent
Kim

(10) Patent No.: US 9,072,721 B2
(45) Date of Patent: Jul. 7, 2015

(54) COMPOSITION FOR PREVENTING OR TREATING IMMUNE-RELATED DISEASE AND OXIDATIVE-STRESS-RELATED DISEASE

(71) Applicant: Hak Bum Kim, Anseong-si (KR)

(72) Inventor: Hak Bum Kim, Anseong-si (KR)

(73) Assignee: Hak Bum Kim, Anseong-si, Gyeonggi-do (KR)

( * ) Notice: Subject to any disclaimer, the term of this patent is extended or adjusted under 35 U.S.C. 154(b) by 0 days.

(21) Appl. No.: 14/382,800

(22) PCT Filed: Mar. 27, 2013

(86) PCT No.: PCT/KR2013/002556
§ 371 (c)(1),
(2) Date: Sep. 4, 2014

(87) PCT Pub. No.: WO2013/147513
PCT Pub. Date: Oct. 3, 2013

(65) Prior Publication Data
US 2015/0017253 A1    Jan. 15, 2015

(30) Foreign Application Priority Data

Mar. 29, 2012    (KR) ........................ 10-2012-0032471

(51) Int. Cl.
| | |
|---|---|
| A61K 36/00 | (2006.01) |
| A61K 36/714 | (2006.01) |
| A61K 33/36 | (2006.01) |
| A61K 31/555 | (2006.01) |
| A61K 33/06 | (2006.01) |
| A61K 33/28 | (2006.01) |
| A61K 35/413 | (2015.01) |
| A61K 35/50 | (2015.01) |
| A61K 35/646 | (2015.01) |
| A61K 36/18 | (2006.01) |
| A61K 36/61 | (2006.01) |
| A61K 35/64 | (2015.01) |

(52) U.S. Cl.
CPC ............... *A61K 33/36* (2013.01); *A61K 31/555* (2013.01); *A61K 33/06* (2013.01); *A61K 33/28* (2013.01); *A61K 35/413* (2013.01); *A61K 35/50* (2013.01); *A61K 35/646* (2013.01); *A61K 36/18* (2013.01); *A61K 36/61* (2013.01); *A61K 36/714* (2013.01); *A61K 35/64* (2013.01)

(58) Field of Classification Search
None
See application file for complete search history.

(56) References Cited

FOREIGN PATENT DOCUMENTS

| | | |
|---|---|---|
| JP | 2008-201765 | 9/2008 |
| KR | 10-1995-0000165 | 1/1995 |
| KR | 10-2000-0015793 | 3/2000 |
| KR | 10-0272835 | 11/2000 |
| KR | 10-2006-0104408 | 10/2006 |
| KR | 10-2010-0055638 | 5/2010 |
| WO | WO 2013/147513 | 10/2013 |

OTHER PUBLICATIONS

International Search Report Dated Jul. 3, 2013 From the Korean Intellectual Property Office Re. Application No. PCT/KR2013/002556 and Its Translation Into English.

*Primary Examiner* — Qiuwen Mi

(57) ABSTRACT

The present invention relates to a composition for preventing or treating an immune-related disease, and, more specifically, relates to a composition for preventing or treating immune-related diseases or oxidative-stress-related diseases in which the toxicity of an arsenic compound is effectively suppressed while the immune function boosting effect thereof is nevertheless maximized. The composition according to the present invention is useful in preventing or treating various immune-related diseases or oxidative-stress-related diseases since the composition reduces the toxicity of arsenic compounds, which traditionally have been difficult to use in clinical practice due to toxicity, while nevertheless maximizing the pharmacological effects thereof.

13 Claims, 12 Drawing Sheets

FIG. 3a
FIG. 3b
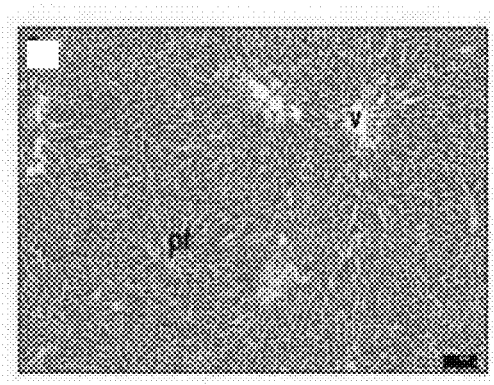
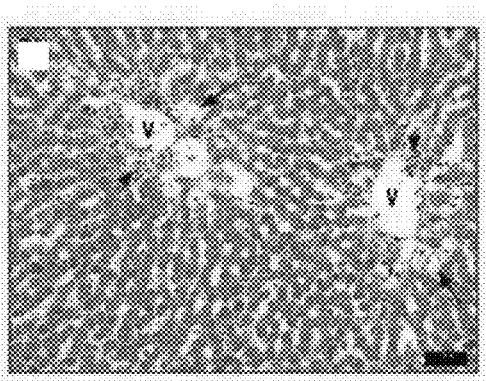
FIG. 4a
FIG. 4b
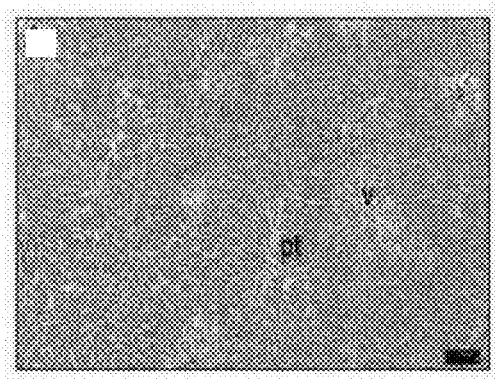
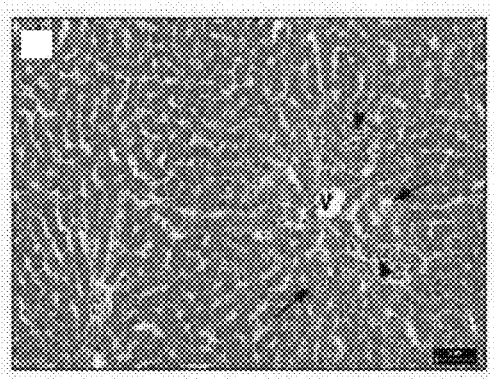

FIG. 12A FIG. 12B FIG. 12C
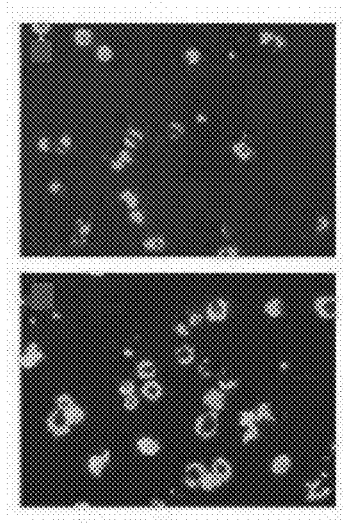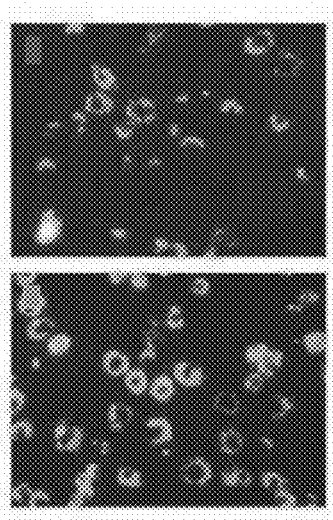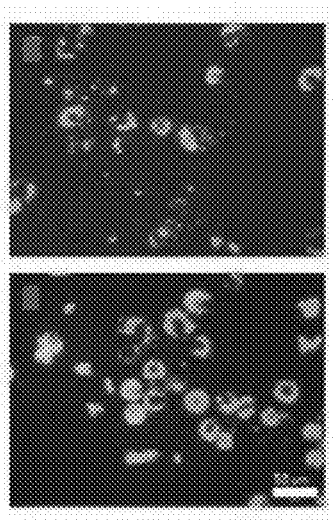
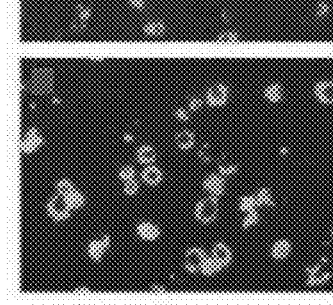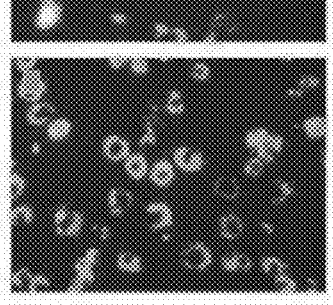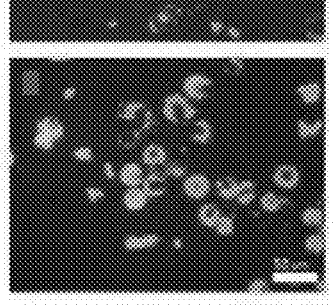
FIG. 12D FIG. 12E FIG. 12F

COMPOSITION FOR PREVENTING OR TREATING IMMUNE-RELATED DISEASE AND OXIDATIVE-STRESS-RELATED DISEASE

RELATED APPLICATIONS

This application is a National Phase of PCT Patent Application No. PCT/KR2013/002556 having International filing date of Mar. 27, 2013, which claims the benefit of priority of Korean Patent Application No. 10-2012-0032471 filed on Mar. 29, 2012. The contents of the above applications are all incorporated by reference as if fully set forth herein in their entirety.

TECHNICAL FIELD

The present invention relates to a composition for preventing or treating immune related diseases or oxidative stress related diseases and, more particularly, to a composition for preventing or treating immune related diseases in which the toxicity of arsenic compounds is effectively inhibited while the immune function boosting effect and antioxidant effect thereof are maximized.

BACKGROUND ART

Immune related diseases and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these. Many immune related diseases are known and have been extensively studied. Such diseases include, for example, immune-mediated inflammatory diseases, non-immune-mediated inflammatory diseases, infectious disease, immunodeficiency disease, etc. It is known that a reduction in immune function leads to various diseases including cancer because a homeostasis maintaining a balance of a living body is broken by not properly treating an antigen from the outside. Particularly, it is reported that the immune function is gradually reduced with age and thus, a possibility of getting a cancer is increased, particularly an incidence of a cancer of liver and respirator system is greatly increased.

Furthermore, the antioxidation refers to the prevention of several oxidations occurring in a human body. The lipid present as a bio-membrane or a lipoprotein is attacked by free radicals occurring in a living body to form many kinds of peroxides. The peroxides and degradation products have a high reactivity and thus allow the structure and function of peripheral biomolecules to change, thereby leading to several chronic diseases. There are several antioxidation defense systems in vivo which can neutralize these free radicals and protect the body. However, when these antioxidation defense systems are lowered to the extent that they cannot adjust the creation of free radicals, oxidative stress and injury of the tissue are facilitated, and excessive free radicals and lipid peroxides produced in vivo lead to an increase of insult due to an oxidative stress such as an oxidation of protein and an injury of DNA (see Kumar C T., et al., *Mol. Cell Biochem.*, 111, pp. 109-115, 1992). It is known that the reactive oxygen species (ROS) can be a main cause of inducing chronic degenerative diseases such as cardiovascular diseases, diabetes, cancers, degenerative neuropathy and aging and that the antioxidants can help in the prevention of chronic degenerative diseases (Bray, T. M. *Nutrition*. 16, pp. 578-581, 2000).

On the other hand, arsenic has been known as a potent carcinogen, affecting skin and lung often, but it is a medicine used for the treatment of human diseases from about 2000 BC. In traditional Chinese medicine including Korean medicine, arsenic compounds had been prescribed for a long time to treat some fatal diseases. In old medical literatures of Korea and China, TongEuiBoGam describes that arsenic was prescribed as an oriental medicine by the name of Bisang and that arsenic was effective in managing choongak or vomiting when it was used after removal of its toxicity. Also, in an old literature of Chinese medicine (BonChoKangMok), the usage and pharmacological actions of arsenic by the name of HwangWoong are described.

Further, in Western medicine, it is described by Hippocrates, 460-377 BC and Galen, 130-200 AD that arsenic compounds were prescribed as a medicine for treating some diseases. Arsenic compounds were prescribed for treating several diseases, including rheumatism, syphilis, psoriasis, etc. and a low concentration of arsenic compounds had been known to act as a beneficial effect on physiological functions of a human body, including stimulation of hematopoiesis. The physiological activities of arsenic as set forth above had been recognized for a long time and actually used for clinical purposes. However, in Korea, arsenic has been regulated as a heavy metal and its use became very limited.

Recently, based on these pharmacological properties of arsenic, attempts to clinically apply them to an anti-cancer drug have been actively made. It was published in 1997 that arsenic trioxide ($As_2O_3$), a kind of arsenic compound, had an excellent effect in treating acute promyelocytic leukemia (see Shen Z X et al., *Blood*, 98: 3354-3360, 1997). Subsequently, its efficacy was demonstrated. Further, in Korean Patent Application No. 1998-16486, it is described in detail that, in the in vivo experiment using a mouse model, the arsenic compounds exhibit activities to inhibit the growth of malignant tumor and effectively inhibit tumor metastasis.

However, the above mentioned research results have suggested possibilities which can be used as a new medicine of arsenic compounds such as arsenic trioxide, but there remains still a need to ameliorate the toxicity of arsenic compounds which can be incurred in an actual application to a human body, and the susceptibility to arsenic at a low concentration.

SUMMARY OF INVENTION

Accordingly, an object of the present invention is to provide a composition for preventing or treating immune related diseases or oxidative stress related diseases in which the toxicity of arsenic compounds is effectively inhibited while the pharmacological effects thereof are increased.

In order to accomplish the above object, the present invention provides a composition for preventing or treating immune related diseases or oxidative stress related diseases in which the toxicity of arsenic compounds is effectively reduced, comprising *Eugenia caryophyllate*, Scorpion, Cinnabar, *Bos taurus* va. *domesticus* Gmelin, *Bombyx* Batryticatus, *Aconitum koreanum* R. Raymund, Alunitum Siccus., *Hominis* Placenta, Borneolum syntheticum and arsenic compounds.

The present invention also provides an antioxidant composition or a composition for the reduction in toxicity of arsenic compounds which comprises *Eugenia caryophyllate*, Scorpion, Cinnabar, *Bos taurus* va. *domesticus* Gmelin, *Bombyx* Batryticatus, *Aconitum koreanum* R. Raymund, Alunitum Siccus., *Hominis* Placenta, Borneolum syntheticum and arsenic compounds.

The composition according to the present invention can reduce the toxicity of arsenic compounds which have traditionally been difficult to use in clinical practice due to toxicity, and also maximize the pharmacological effects thereof. By doing so, the present composition is effective in preventing or treating a various range of immune related diseases including a hepatitis, a liver cirrhosis, a cancer, an acquired immune deficiency syndrome, an asthma and an atopy through the immune function boosting effect thereof. Further, the present composition is useful in preventing or treating oxidative stress related diseases through an antioxidant effect of arsenic compounds.

DESCRIPTION OF DRAWINGS

The above and other objects and features of the present invention will be apparent from the below descriptions with reference to the accompanying drawings:

FIGS. 3*a-b* are photographs in which a histopathological lesion of a rat liver pre-treated with a low dose sample (pill of Example 1) and a carbon tetrachloride is identified by a hematoxylin eosin staining.

FIGS. 4*a-b* are photographs in which a histopathological lesion of a rat liver pre-treated with a high dose sample (pill of Example 1) and a carbon tetrachloride is identified by a hematoxylin eosin staining.

FIGS. 12A-F are graphs confirming the influence on the phagocytosis of sample in macrophage (pill of Example 1) (A: untreated group, B: LPS treated group, C: LPS+sample 10 µg/ml treated group, D: LPS+sample 50 µg/ml treated group, E: LPS+sample 100 µg/ml treated group and F: LPS+sample 200 µg/ml treated group).

DETAILED DESCRIPTION

Figure 1A:
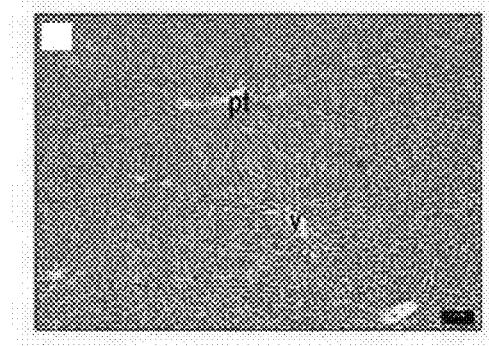
FIGS. 1*a-b* are photographs in which a histopathological lesion of a normal rat liver is identified by a hematoxylin eosin staining. Here, pt represents a portal triad and V represents a central vein.

The present invention will be now described in detail.

The present invention relates to a composition for preventing or treating immune related diseases or oxidative stress related diseases in which the toxicity of arsenic compounds is effectively reduced, comprising *Eugenia caryophyllate*, Scorpion, Cinnabar, *Bos taurus* va. *domesticus* Gmelin, *Bombyx mori* Linne, *Aconitum koreanum* R. Raymund, Alunitum Siccus., *Hominis* Placenta, Borneolum syntheticum and arsenic compounds.

As used herein, the term "immune related diseases" refers to diseases wherein any constituent in a mammal immune system induces or mediates diseases in the mammal or contributes to the incidence rate thereof. Also, the immune related diseases include diseases having the effect of accelerating the progress of diseases through stimulation or intervention of the immune reaction. The above immune related diseases further comprise immune mediated inflammatory diseases, non-immune mediated inflammatory diseases, infectious diseases, immune deficiency diseases, neoplasia and the like.

Specific examples of the immune related diseases which can be treated in accordance with the present invention include, but not limited to, an inflammatory disease such as an acquired immune deficiency syndrome (AIDS), a hepatitis and a liver cirrhosis, and an allergic disease such as each type of cancer, an asthma, an allergic rhinitis, an atopic dermatitis, a food hypersensitivity and a hives.

On the other hand, the term "oxidative stress related diseases" as used herein refers to diseases caused by active oxygen species (free radical) incurred in a living body during the process in which an oxygen and a nutritional substance are reacted and metabolized. Specifically, the oxidative stress related diseases comprises, for example, lipid metabolism diseases such as hyperlipidemia, heart diseases such as vascular sclerosis, heart failure, hypertensive heart failure, arrhythmia, myocardial infarction and angina pectoris, ageing, immune diseases and cancer.

Each component of the composition according to the present invention are illustrated as follows.

Arsenic compounds used in the present invention refer to the arsenic compounds which can be pharmaceutically used. Examples thereof comprise, but not limited to, arsenic trioxide ($As_2O_3$), arsenic hexoxide ($As_4O_6$), arsenic tribromide ($AsBr_3$), arsenic trichloride ($AsCl_3$), arsenic triiodide ($AsI_3$) and melarsoprol, named Bisang.

*Eugenia caryophyllate* used in the present invention is buds of clove tree (*Syringa velutina* var. *kamibayshii*) of tropical evergreen arborescence, and the powder or oil thereof are used for edible and medicinal purposes. *Eugenia caryophyllate* is prescribed to treat vomiting, gastric cancer, abdominal pain, dyspepsia, sexual dysfunction, gingival inflammation, gingival pain and the like. The pharmacological action thereof is reported to have gastric juice secretion promotion, analgesia, anticonvulsant, anti-inflammatory, antioxidant, antithrombotic, antibacterial, helminthic and antihypertensive activities.

Scorpion used in the present invention refers to that obtained by drying the body of Scorpion belonging to Scorpion family. Scorpion have an expectorant action and also have functions to treat facial paralysis and remove stroke.

Cinnabar used in the present invention consists of a crystal and is a natural ore comprising as a main component a sulfur compound such as mercuric sulfide (HgS). Cinnabar has functions to promote a mental stability, stop a convulsion, lower a heat and neutralize a poison. Cinnabar is prescribed to treat symptoms such as a startle, a palpitation, a sleep disorder, an amnesia, a convulsion, an epilepsy, a psychosis, a high fever, a mental confusion or a delirium.

*Bos taurus* var. *domesticus* Gmelin used in the present invention is an aggregate which is abnormally provided within a gall bladder of ruminants such as cattle, goat and antelope inhabited in India, Iran, China and the like. This is used by mainly extracting from a gall bladder or a bile duct of the cattle, removing the membranous outside and drying under the shade. The appearance is a small lump of yellowish brown sphere with a diameter of about 2 cm which is light and easily broken. The taste is a little bitter. The main component thereof includes colic acid, bilirubin, ergosterol, vitamin D and the like. In Chinese medicine, it is used as an antipyretic drug, an antidote, a sedative, an analgesic and a cardiotonic agent.

*Bombyx* Batryticatus used in the present invention refers to that wherein a silkworm, *Bombyx mori* L. is spastically killed by infection of *Beauveria bassiana* (Bals.) Vuill before its spinning and then dried. *Bombyx* Batryticatus has a function to remove stroke and moisture, an expectoration action, and a function to remove a poison of the swelling.

*Aconitum koreanum* R. Raymund used in the present invention refers to a tuber of perennial *Aconitum koreanum*, *Typhonium giganteum* belonging to Buttercup family. This is prescribed to remove stroke and sputum to thereby treat a facial paralysis due to stroke, a convulsion, a crisis (fit), a stroke, a tetanus, a migraine, a headache, a neuralgia quadriplegia, an arthralgia, a scrotal eczema, a skin itch and a cervical lymphadenitis. Further, it has a detoxification faction when bitten by a snake.

Alunitum Siccus. used in the present invention refers to an alum. That is, this is obtained by heating and dehydrating potassium alum (KAI $(SO_4)_2.12H_2O$). Alunitum Siccus. is used as a medicine such as a hemostatic and a restringent. Further, this is known to have a de-hydrating action.

*Hominis* Placenta used in the present invention is a human placenta, non-toxic, and mainly prescribed as a roborant (tonic) to treat a chronic fatigue syndrome, a neurasthenia, an anemia, a chronic bronchitis, an asthma, a cough and a tuberculosis. Further, this has functions to contract womb and facilitate the development of milk line and feminine generative organs.

Borneolum syntheticum used in the present invention refers to a white crystal obtained by slicing a resin or tree trunk of a tall evergreen tree, *Dryobalanops aromatica* GAERTNER, belonging to Dipterocarpaceae family and steam-distilling the same. Borneolum syntheticum is effective for the treatment of a mental confusion and a disturbance of consciousness, for the lowering of a heat and swelling, for the alleviation of a pain, and for the treatment of a high fever, a convulsion and an epilepsy in childhood. This is also used to treat each kind of inflammations including pharyngolaryngitis, stomatitis, ophthalopathy, itch, hyperemia, and inflammation of eye and nose.

The composition according to the present application may comprises a therapeutically effective amount of *Eugenia caryophyllate*, Scorpion, Cinnabar, *Bos taurus* va. *domesticus* Gmelin, *Bombyx* Batryticatus, *Aconitum koreanum* R. Raymund, Alunitum Siccus., *Hominis* Placenta, Borneolum syntheticum and arsenic compounds, respectively.

The composition according to the present invention comprises, preferably, 1 through 7 parts by weight of arsenic compounds, 15 through 25 parts by weight of *caryophyllate*, 200 through 270 parts by weight of Scorpion, 20 through 30 parts by weight of Cinnabar, 25 through 35 parts by weight of *Bos taurus* va. *domesticus* Gmelin, 50 through 65 parts by weight of *Bombyx mori* Linne, 38 through 48 parts by weight of *Aconitum koreanum* R. Raymund, 50 through 65 parts by weight of Alunitum Siccus., 200 through 270 parts by weight of *Hominis* Placenta, and 0.5 through 6 parts by weight of Borneolum syntheticum.

The composition according to the present invention comprises, more preferably, 3 through 5 parts by weight of arsenic compounds, 17 through 22 parts by weight of *caryophyllate*, 220 through 250 parts by weight of Scorpion, 22 through 27 parts by weight of Cinnabar, 27 through 31 parts by weight of *Bos taurus* va. *domesticus* Gmelin, 55 through 62 parts by weight of *Bombyx mori* Linne, 41 through 46 parts by weight of *Aconitum koreanum* R. Raymund, 55 through 62 parts by weight of Alunitum Siccus., 220 through 250 parts by weight of *Hominis* Placenta, and 2 through 4 parts by weight of Borneolum syntheticum.

The composition for preventing or treating immune related diseases according to the present invention may be formulated in various kinds of forms for oral or parenteral administrations. Examples of the composition for oral administration may include tablets, capsules, granules, pills and the like.

Such composition according to the present invention may be prepared in combination with pharmaceutically acceptable carriers, diluents or excipients. Suitable carriers, diluents or excipients used herein may include, for example, excipients such as starch, sugar and mannitol; fillers and extenders such as calcium phosphates and silicic acid derivatives; cellulose derivatives such as carboxymethyl celluloses or hydroxypropyl celluloses; binders such as gellatin, alginate or polyvinyl pyrrolidone; lubricants such as talc, calcium stearate, magnesium stearate, hydrogenated castor oil, and solid polyethylene glycol; disintegrants such as povidone, crosscarmellose sodium and crosspovidone; and surfactants such as polysorbate, cetyl alcohol, and glycerol monostearate. Further, when the composition is a pill, a binder such as a honey can be included in order to combine with the component of the pill.

In order to prevent a mutual adhesion of the prepared pill, an occurrence of mold and an evaporation of water, or conduct the mating or flavoring, dusting powders such as lycopodium powder, talc, starch, kaolin, licorice powder, cinnamon powder and orrisroot can be included.

In addition, various range pharmaceutical compositions comprising a predetermined amount of active ingredients with or without additives such as the carrier, diluent or excipient can be prepared in accordance with a known conventional method. For example, when the above composition is prepared in the form of tablet, the additives such as a carrier, a diluent or an excipient can be added to the composition and a compression molding is then conducted directly or after making a granular. In the case of capsules, the above composition can be filled in the capsules in the form of liquid, suspension or granular or encapsulated in a capsule base. In the case of the pill, the additives such as a carrier, a diluent or an excipient can be added to the composition and uniformly mixed to make a plastic mass. The resulting mass is then divided and molded into a spherical shape to make the desired pill.

The composition of the present invention thus obtained exhibits excellent effects capable of significantly reducing the toxicity of the conventionally known arsenic compounds as can be confirmed from the following examples. Also, the composition of the present invention exhibits significant effects in the prevention or treatment of immune related diseases by maximizing the immune function boosting effect of arsenic compounds. Further, the compositions of the present invention exhibits excellent antioxidant effects and thus are useful for the prevention or treatment of various oxidative stress related diseases including lipid metabolism diseases such as hyperlipidemia, heart diseases such as vascular sclerosis, heart failure, hypertensive heart diseases, arrhythmia, myocardial infarction and angina pectoris, ageing, immune diseases and cancer.

The present invention will be described in detail with reference to the following examples. The examples are intended be only illustrative, but are not to be construed as limiting the present invention.

Example 1

Preparation of Pills Containing Arsenic Compounds

In order to prepare the pill containing arsenic compound according to the present invention, each medicinal ingredients (Bisang (arsenic trioxide) as an arsenic compound; *Eugenia caryophyllate*; Scorpion; Cinnabar; *Bos taurus* va. *domesticus* Gmelin; *Bombyx* Batryticatus; *Aconitum koreanum* R. Raymund; Alunitum Siccus.; *Hominis* Placenta; and Borneolum syntheticum) were selected and purchased from GyeongDong Market in Seoul. Subsequently, 40 g of Bisang, 200 g of *Eugenia caryophyllate*, 2400 g of Scorpion; 250 g of Cinnabar, 300 g of *Bos taurus* va. *domesticus* Gmelin, 600 g of *Bombyx* Batryticatus, 450 g of *Aconitum koreanum* R. Raymund, 600 g of Alunitum Siccus., 2400 g of *Hominis* Placenta, and 30 g of Borneolum syntheticum were weighted, respectively, pulverized and then mixed by a mixer (G&S Korea). To allow the mixed medicinal ingredients to combine together, an appropriate amount of honey was added to make dough. The dough thus obtained was drawn from a pill making machine (order-produced from DaeSung Pharmaceutical Machine Factory, PM TECH Automatic Machine) and then put into a pill cutting machine (order-produced from DaeSung Pharmaceutical Machine Factory, PM TECH Automatic Machine) to make a pill. The pill thus prepared was used in the experiments below.

Experiment Example 1

Analysis of Liver Protective Effect and Safety

Carbon tetrahydrochloride ($CCl_4$) is a typical hepatotoxic chemical substance which is widely used for the research associated with a liver cell injury. Carbon tetrahydrochloride accumulates a free radical produced during the enzymatic metabolism procedure in a liver cell to thereby induce a cell injury with oxidative stress caused by a lipid peroxidation of cellular membrane, an oxidative modification of protein or s DNA damage.

Accordingly, in order to determine a liver protective effect of the pharmaceutical composition according to the present invention, the pill prepared in Example 1 was administered to a white rat simultaneously with the administration of carbon tetrahydrochloride. Subsequently, the serological index or histopathologic deformation from the liver cell damage, and lipid peroxidation level associated with the oxidative stress were compared and the defense effect to the liver cell injury of the pill provided and the safety after the oral administration thereof were identified.

Laboratory Animal

Eight week-aged male Spargue-Dawley rats (Samtako, Korea) were purchased and accommodated for 5 days under the temperature 23±1° C., humidity 50±5% and 12 hour light/12 hour dark condition in the Sanitary Animal Breeding Facilities of Semyung University, Korea. When their weights reached the average of 235 g, the rats was used for the experiments. During the entire experiment period, the feed (from JeilJedang, Korea) and drink were freely available. The animal experiments were carried out with the approval (smeac 11-08-01) of the Animal Experiment Ethics Commission of Semyung University.

Classification and Treatment of Experiment Groups

Normal Group was orally administered with 1 ml of distilled water daily for 7 days from the experiment start day. After 1 hour of the final administration, olive oil (1 ml/kg body weight) was intraperitoneally administered.

Control Group was orally administered with 1 ml of distilled water daily for 7 days from the experiment start day. After 1 hour of the final administration, $CCl_4$ solution (50% $CCl_4$ in olive oil) (1 ml kg body weight) was intraperitoneally administered.

Low-dose Group was orally administered with low-dose pill solution (300 mg/kg body weight) daily for 7 days from the experiment start day. After 1 hour of the final administration, $CCl_4$ solution (50% $CCl_4$ in olive oil) (1 ml/kg body weight) was intraperitoneally administered.

High-dose Group was orally administered with a high-dose pill solution (1500 mg/kg body weight) daily for 7 days from the experiment start day. After 1 hour of the final administration, $CCl_4$ solution (50% $CCl_4$ in olive oil) (1 ml/kg body weight) was intraperitoneally administered.

Silymarin Group was orally administered with Silymarin solution (Sigma Co., USA)(100 mg/kg body weight) daily for 7 days from the experiment start day. After 1 hour of the final administration, $CCl_4$ solution (50% $CCl_4$ in olive oil) (1 ml/kg body weight) was intraperitoneally administered.

Safety Test Group was orally administered with a high-dose pill solution (1500 mg/kg body weight) daily for 7 days from the experiment start day in the same manner as Normal Group in order to evaluate the safety of the pill provided. After 1 hour of the final administration, olive oil (1 ml/kg body weight) was intraperitoneally administered.

The classification and experiment procedure of the above Test Groups are schematically shown in Table 1 below.

TABLE 1

| | 1 day | 2 day | 3 day | 4 day | 5 day | 6 day | 7 day | 8 day |
|---|---|---|---|---|---|---|---|---|
| Normal Group (n = 12) | W | W | W | W | W | W | Δ W | ↓ |
| Control Group (n = 12) | W | W | W | W | W | W | ▲ W | ↓ |
| Low-dose Group (n = 12) | ○ | ○ | ○ | ○ | ○ | ○ | ▲ ○ | ↓ |
| High-dose Group (n = 12) | ● | ● | ● | ● | ● | ● | ▲ ● | ↓ |
| Silymarin Group (n = 12) | ◇ | ◇ | ◇ | ◇ | ◇ | ◇ | ▲ ◇ | ↓ |
| Safety Test Group (n = 12) | ● | ● | ● | ● | ● | ● | Δ ● | ↓ |

Δ: olive oil/1 ml/kg (body weight) intraperitoneal administration
▲: 50% $CCl_4$/1 ml/kg (body weight) intraperitoneal administration
W: Distilled water/1 ml oral administration
○: low-dose sample/300 mg/kg (body weight) oral administration
●: high-dose sample/1,500 mg/kg (body weight) oral administration
◇:: Silymarin/300 mg/kg (body weight) oral administration
↓: Sacrificed Inspection Item 1) Weight and Weight Gain Rate The weights of all test animals were measured at 4 days, 7 days and the experiment end date (8 days) from the experiment start date (1 day). The weight gain rates thereof were calculated by (weight gain for 7 days/weight at the experiment start day)×100.

2) Measurement of Liver Weight and Liver/Weight Ratio

The autopsy of the test animals was conducted to extract the livers. The peripheral connective tissues were carefully removed and the liver weight was then measured. Liver/weight ratio was calculated by (liver weight/weight)×100.

3) Activity Inspection of Serum Alanine Aminotransferase and Aspartate Aminotransferase Olive oil or $CCl_4$ was intraperitoneally administered to white rats. The white rats were lightly anesthetized with ether and the blood was collected through heart and then introduced in serum separation tube. The serum separation tube was centrifuged at a speed of 3,500 rpm for 10 minutes under cold-storage state to separate the serum. Serum alanine aminotransferase (ALT) and aspartate aminotransferase (AST) were measured by Modified IFCC method using automatic biochemistry analyzer (Hitachi modulator, Japan). The reagents used in the measurement were AST (Roche, USA) and ALT (Roche, USA).

4) Measurement of Lipid Peroxidation Level in Liver Tissue

The weight of liver was measured and a part of right site of the median lobe was then extracted and used for the measurement of lipid peroxidation level in the liver tissue.

The measurement of lipid peroxidation level was carried out in accordance with Ohkawan method (Ohkawa et al., J. Med. Chem., 40, pp. 559-573, 1997). Malondialdehyde, a final product of lipid peroxidation, was quantified as an index using Thiobarbituric acid assay. That is, the liver tissue was homogenized with 10 fold (v/w) dose of 1.15% potassium chloride solution to prepare a homogenized liquid. 0.2 ml of the homogenized liquid was then mixed with 0.2 ml of 8.1% sodium dodecyl sulfate (SDS), 1.5 ml of 20% acetic acid (pH 3.5), 0.5 ml of 5% butylated hydroxytoluene and 1.5 ml of 0.8% thiobarbituric acid. The mixture was reacted for 60 minutes in a thermostat at 100° C. The reaction was then left at room temperature for 1 hour and centrifuged at 3,000 rpm for 10 minutes to take a supernatant liquid. The absorbance thereof was measured with UV spectroscopy at 532 nm.

5) Histopathologic Inspection of Liver Tissue

The left site of the extracted median lobe was fixed to 10% neutral buffered formaline (NBF) solution for one day, and general alcohol dehydration and xylene transparency process were conducted to make a paraffin block. The paraffin thin fragment with a thickness of 5 μm was prepared and the hematoxylin eosin staining was carried out. The pathological findings were compared and observed with optical microscope.

CONCLUSION

A. Liver Protective Effect

1) Difference of Weight

The weight in the normal group was constantly increased for the experiment period. The weigh was reduced at 8 day of the experiment due to fasting.

In the control group, the weight gain was observed up to 7 day of the experiment in a similar level to the normal group. However, due to the fasting and $CCl_4$ administration, the weight gain was significantly lowered at 8 day of the experiment as compared with the normal group, and the weight gain rate was significantly lowered as compared with the normal group.

In the low-dose group, the high-dose group and the silymarin group, the weight and weight gain rate were a little higher as compared with the control group, but there were no significant differences (Table 2).

TABLE 2

Influence on the pretreatment of sample material on the weight in $CCl_4$-induced hepatotoxicity of rats

| | Weight (g) | | | | |
|---|---|---|---|---|---|
| Group | 1 day | 4 day | 7 day | 8 day | Weight gain rate (%) |
| Normal Group (n = 12) | 236 ± 6 | 259 ± 7 | 281 ± 9 | 272 ± 9 | 15.5 ± 2.5 |
| Control Group (n = 12) | 234 ± 4 | 258 ± 5 | 279 ± 8 | 259 ± 8** | 10.8 ± 2.2*** |
| Low-dose Group (n = 12) | 235 ± 9 | 257 ± 12 | 282 ± 14 | 265 ± 12 | 12.3 ± 4.2 |

TABLE 2-continued

Influence on the pretreatment of sample material on the weight in $CCl_4$-induced hepatotoxicity of rats

| Group | Weight (g) | | | | Weight gain rate (%) |
|---|---|---|---|---|---|
| | 1 day | 4 day | 7 day | 8 day | |
| High-dose Group (n = 12) | 237 ± 4 | 260 ± 5 | 284 ± 5 | 265 ± 5 | 11.7 ± 3.1 |
| Silymarin Group (n = 12) | 236 ± 5 | 261 ± 4 | 284 ± 5 | 263 ± 6 | 11.7 ± 2.2 |

Each reference number shows mean ± SD value for each of seven rats
*shows a statistically significant effect as compared with the normal group (*$p < 0.001$; $p < 0.01$)

2) Difference of Liver Weight and Liver/Weight Ratio

The liver weight and liver/weight ratio measured at the experiment end day showed that the control group is significantly higher as compared with the normal group.

In the low-dose group, both the liver weight and liver/weight ratio were significantly higher as compared with the control group.

In the high-dose group and silymarin group, the liver weight and liver/weight ratio were a little lower as compared with the control group, but there being no significant difference (Table 3).

TABLE 3

Influence on the pretreatment of sample material on the liver weight and liver/weight ratio in $CCl_4$-induced hepatotoxicity of rats

| Group | Liver weight (g) | Liver/weight ratio (%) |
|---|---|---|
| Normal Group (n = 12) | 8.66 ± 0.70 | 3.18 ± 0.22 |
| Control Group (n = 12) | 10.38 ± 0.61*** | 4.00 ± 0.26*** |
| Low dose Group (n = 12) | 9.77 ± 0.56# | 3.71 ± 0.25# |
| High dose Group (n = 12) | 10.33 ± 0.61 | 3.79 ± 0.24 |
| Silymarin Group (n = 12) | 10.22 ± 0.61 | 3.88 ± 0.27 |

Each reference number shows mean ± SD value for each of seven rats
*shows a statistically significant effect as compared with the normal group (***$p < 0.001$)
shows a statistically significant effect as compared with the control group (#$p < 0.05$)

3) Difference of Blood ALT and AST Activities

The blood ALT and AST activities of the control group are significantly higher as compared with those of the normal group.

The blood ALT of the low-dose group was significantly lower as compared with the control group. The blood AST of the low-dose group was significantly lower as compared with those of the control group, but the significant differences were not observed.

The blood ALT and AST of the high-dose group were significantly lower as compared with those of the control group.

Even in the silymarin group, the blood ALT was significantly lower as compared with the control group, but the significant differences were not observed (Table 4).

TABLE 4

Influence on the pretreatment of sample material on the blood ALT and AST activities in $CCl_4$-induced hepatotoxicity of rats

| Group | Blood ALT (IU/L) | Blood AST (IU/L) |
|---|---|---|
| Normal Group (n = 12) | 44.8 ± 5.3 | 85.5 ± 26.6 |
| Control Group (n = 12) | 375.8 ± 207.8*** | 657.4 ± 333.4*** |
| Low-dose Group (n = 12) | 196.0 ± 143.1# | 384.9 ± 325.3 |
| High-dose Group (n = 12) | 178.7 ± 106.3## | 401.2 ± 211.5# |
| Silymarin Group (n = 12) | 229.8 ± 107.2# | 520.1 ± 300.6 |

Each reference number shows mean ± SD value for each of seven rats
*shows a statistically significant effect as compared with the normal group (***$p < 0.001$)
shows a statistically significant effect as compared with the control group (##$p < 0.01$; #$p < 0.05$)

4) Differences of Lipid Peroxide Level in Liver Tissue

The level of malondialdehyde (MDA), i.e., lipid peroxide in the liver tissue of the control group, was significantly higher as compared with the normal group.

In contrast, in the low-dose group, high-dose group and silymarin group, the MDA level in the liver tissue was significantly lower as compared with the control group (Table 5).

TABLE 5

Influence on the pretreatment of sample material on the MDA content of the liver tissues in $CCl_4$-induced hepatotoxicity of rats

| Group | MDA (μM/mg protein) |
|---|---|
| Normal Group | 0.75 ± 0.06## |
| Control Group | 1.47 ± 0.16** |
| Low-dose Group | 0.75 ± 0.08## |
| High-dose Group | 0.34 ± 0.04### |
| Silymarin Group | 0.27 ± 0.06### |

Each reference number shows mean ± SD for each of seven rats
*shows a statistically significant effect as compared with the normal group (**$p < 0.01$)
shows a statistically significant effect as compared with the control group (###$p < 0.001$; ##$p < 0.01$)

5) Difference of Histopathologic Findings

Figure 1B:
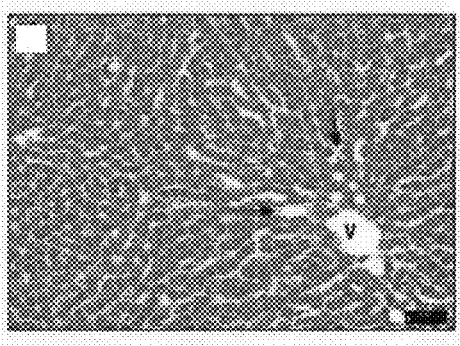
Figure 2A:
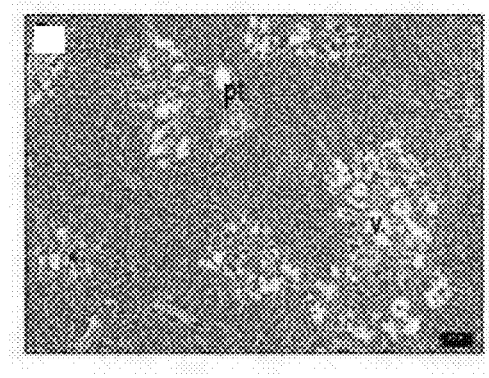
FIGS. 2*a-b* are photographs in which a histopathological lesion of a control group rat liver treated with a carbon tetrachloride is identified by a hematoxylin eosin staining.
Figure 2B:
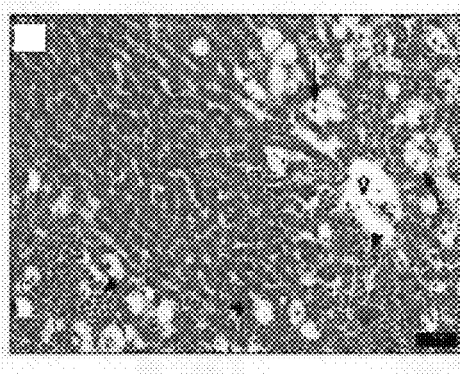

The liver tissue of the normal group maintained showed that all tissues of the central vein, portal trigone, liver cell plate and oriental capillary were well maintained as shown in FIGS. 1(a) and 1(b) and that the liver cell also took a normal tissue. In the liver tissue of the control group, a wide liver cell necrosis around a central vein was observed. In the liver cell around the necrosis, various sizes of vacuolar degeneration and lipid change were observed. In the necrosis site, a large amount of inflammatory cell infiltration was confirmed. The liver cell around the portal trigone maintained a relatively normal tissue (see FIGS. 2(a) and 2(b)).

Figure 5A:
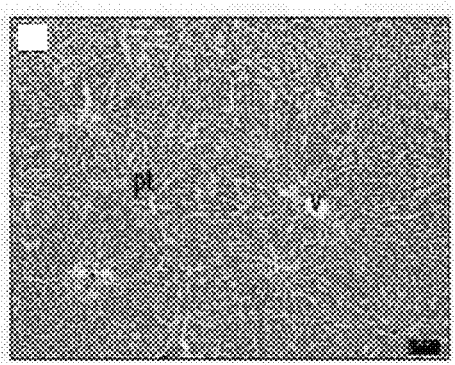
FIGS. 5*a-b* are photographs in which histopathological lesion of a control rat liver pre-treated with silymarin and carbon tetrachloride is identified by a hematoxylin eosin staining.
Figure 5B:
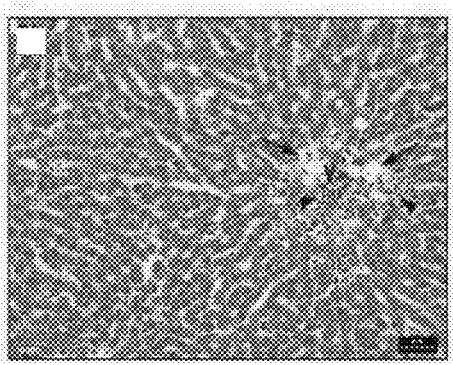

On the other hand, as can be confirmed from FIGS. 3(a) and (b), the histopathologic change of the liver tissue observed in the low-dose group was identical with that of the control group, but the level of liver cell necrosis and degradation around the central vein was very slight and the infiltration level of the inflammation cell was significantly reduced as compared with the control group. Even in the high-dose group, the liver cell necrosis and degradation were confirmed only around the central vein. The infiltration of the inflammation cell was very rarely observed and it was shown to be similar to that of the normal group (see FIGS. 4(a) and 4(b)). In the silymarin group the histopathologic findings and level were observed to be similar to those in the high-dose group (see FIGS. 5(a) and 5(b)).

As set forth above, in the low-dose group (300 mg/weight kg) of the pill from Example 1, the blood ALT was shown to be significant as compared with the control group, and the blood AST was not recognized to have a remarkable difference, but it was shown to be remarkably lower as compared with the control group. Histopathologically, the level of lesion was alleviated as compared with the control group. Also, in the high-dose group (1,500 mg/weight kg) of the above pill, both the blood ALT and AST were remarkably lower as compared with the control group. Histopathologically, the findings and level of lesion were alleviated as compared with the control group. Accordingly, it is considered that the composition of the present invention can prevent a liver cell injury in concentration-dependent, and also effectively prevent and treat the liver diseases such as hepatitis and liver cirrhosis which can be incurred by oxidative stress and the like.

B. Safety Analysis

1) Difference of Weight

In the safety test group for evaluating the safety of the pill prepared in Example 1, the weight and weight gain rate were a little higher as compared with the normal group, but there was no significant difference (Table 6).

TABLE 6

Effects of the weight of rats upon treatment of high-dose sample (safety test group)

| Group | Weight (g) | | | | Weight gain (%) |
|---|---|---|---|---|---|
| | 1 day | 4 day | 7 day | 8 day | |
| Normal group | 196 ± 8 | 218 ± 10 | 237 ± 10 | 239 ± 9 | 21.8 ± 0.9 |
| Safety test group | 196 ± 8 | 217 ± 10 | 241 ± 11 | 242 ± 11 | 23.2 ± 2.4 |

Each reference number shows mean ± SD value for each of seven rats

2) Difference of Liver Weight and Liver/Weight Ratio

In the safety test group for evaluating the safety of the pill prepared in Example 1, the weight and weight gain rate were shown to be similar to those of the normal group (Table 7).

TABLE 7

Effects of the weight of rats upon treatment of high-dose sample (safety test group)

| Group | Liver weight (g) | Liver/Weight ratio (%) |
|---|---|---|
| Normal group | 9.37 ± 0.43 | 3.93 ± 0.12 |
| Safety test group | 9.64 ± 0.76 | 4.00 ± 0.35 |

Each reference number shows mean ± SD value for each of seven rats

3) Differences of the Blood ALT and AST Activities

In the safety test group for evaluating the safety of the pill prepared in Example 1, the blood ALT and AST were shown to be similar to those of the normal group (Table 8).

TABLE 8

Effects of the blood ALT and AST of rats upon treatment of high-dose sample (safety test group)

| Group | Blood ALT (IU/L) | Blood AST (IU/L) |
|---|---|---|
| Normal group | 40.0 ± 4.7 | 73.6 ± 5.6 |
| Safety test group | 36.4 ± 3.7 | 72.3 ± 4.5 |

4) Difference of Lipid Peroxide Level of the Liver Tissue

In the safety test group for evaluating the safety of the pill prepared in Example 1, the MDA level in the liver tissue was significantly lower as compared with the normal group (Table 9).

TABLE 9

Effects of the MDA level in the liver tissue of rats upon treatment of high-dose sample (safety test group)

| Group | MDA (μM/mg protein) |
|---|---|
| Normal group | 0.75 ± 0.06 |
| Safety test group | 0.30 ± 0.08** |

Each reference number shows mean ± SD value for each of seven rats
*shows a statistically remarkable effect as compared with the normal group (**p < 0.01)

5) Difference of Histopathologic Findings

Figure 6A:
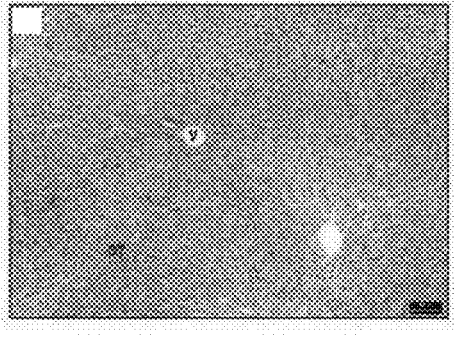
FIGS. 6*a-b* are photographs in which a histopathological lesion of a normal rat liver is identified by a hematoxylin eosin staining.
Figure 6B:
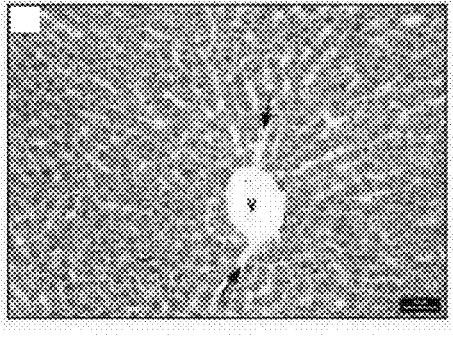
Figure 7A:
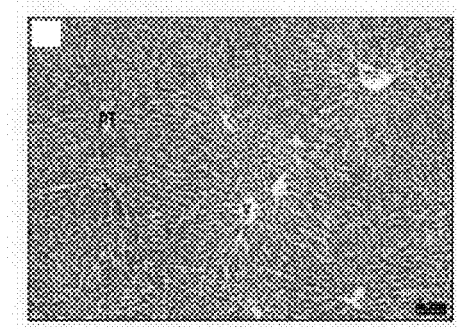
FIGS. 7*a-b* are photographs in which a histopathological lesion of rat liver pre-treated with a high dose sample (pill of Example 1) is identified by a hematoxylin eosin staining.
Figure 7B:
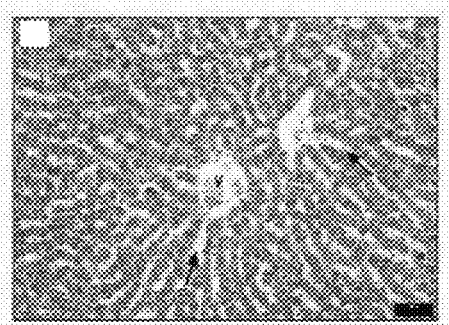

As a result of confirmation, the liver tissue of the normal group showed that all tissues of the central vein, portal trigone, liver cell plate and oriental capillary were well maintained and that the liver cell also took a normal tissue (see FIGS. 6(a) and 6(b)). Even in the safety test group in which a high dose of the pill only was administered, the liver tissue was maintained as a normal tissue (see FIGS. 7(a) and 7(b)).

As set forth above, the result of the safety test of the pill prepared in Example 1 of the present invention showed that, although the pill of the present invention was administered in a high dosage, all items such as weight, liver weight, blood ALT and AST, MDA and histopathologic findings were confirmed to be similar to the normal group and that the pill of the present invention had an excellent safety which does not lead to a liver cell injury.

Experiment Example 2

Analysis of the Antioxidant Effect, Immune Boosting Effect and Immune Related Disease Treatment Effect The experiment for free radical scavenging activity was carried out by the method which can see an antioxidant effect using 2,2-diphenyl-1-picrylhydrazyl(DPPH), a chemically stable free radical. As a result, the DPPH had a maximum absorbance around 515 nm to 520 nm. If this radical met an electron, the radical (DPPH) was eliminated while donating the electron and the color was changed. The chemically stable DPPH could analyze antioxidant effects of an extract containing several kinds of antioxidant ingredients, a drink and oil, a pure phenol compound and the like.

On the other hand, the free radical of the active nitrogen, nitric oxide (NO) leads to the oxidative stress with the active oxygen. Sodium nitrate had the maximum absorbance at 520 nm. If this radical met a substance having antioxidant activity, the radical (DPPH) was scavenged while donating the electron and the color was changed.

Accordingly, in the present experiment, in order to measure the antioxidant efficacy of the pill prepared in Example 1, the free radical scavenging activity was determined using DPPH and sodium nitrate.

In the present experiment, the infiltration action of macrophage was evaluated to determine immune boosting efficacy of the sample. Lipopolysaccharide (LPS) induced the production of nitric oxide and then treated with the pill sample according to the present invention, thereby evaluating the efficacy of inhibiting the production of nitric oxide. Consequently, the efficacy of inhibiting a hypersensitive reaction was evaluated.

Further, the mast cell which is an immune cell mainly caused by allergy was treated with the pill sample according to the present invention to evaluate the efficacy of inhibiting histamine secretion. By doing so, the efficacy of inhibiting an allergy reaction was measured. In order to analyze the effect associated with asthma under allergy reaction, bronchial epithelial cell was stimulated with LPS. The amount of secreted inflammatory cytokine was then measured to thereby evaluate the inhibitory of inhibiting bronchial asthma of the sample.

Material and Method

1) Preparation of Experiment Materials 200 g of the pill prepared in Example 1 was precisely taken to which 2 L of distilled water was added to extract with a hot water. The extract was then condensed using reduced pressure concentrator and lyophilized to obtain a fine powder in a yield of 46.08%. This powder was used as the sample in the subsequent experiment.

2) Evaluation of Antioxidant Functionality 2-1) DPPH Free Radical Scavenging Activity The lyophilized samples were prepared in concentrations of 0.8, 4, 20, 100 and 200 mg/ml to make test solutions. To each well 40 μl of EtOH was added and 2.5 mM DPPH was then added. The mixture was reacted for 30 minutes. The free radical scavenging activity (%) for this reaction solution was calculated by measuring the absorbance at 515 nm.

2-2) NO Analysis

The lyophilized samples were prepared in concentrations of 0.8, 4, 20, 100 and 200 mg/ml to make test solutions. The test solutions (1 ml) were dispensed in 15 ml tubes, respectively. 2 ml of 1 mM sodium nitrate solution were added to each tube, respectively. pH 1.2 of hydrochloric acid solution, pH 3.0 of citric acid buffer solution and pH 6.0 of citric acid buffer solution were added in 7 ml to each tube and reacted at 37° C. for one hour. To 1 ml of this reaction solution, 2% acetic acid solution and Griess reagent were added. The mixture was further reacted for 15 minutes. Nitrous acid scavenging activity (%) was calculated by measuring the absorbance at 520 nm.

3) Cytotoxicity Assay of Sample in Macrophage

RAW 264.7 cell (mouse macrophage) was treated with the samples to confirm the cytotoxicity of samples against the immune cell.

The cells were purchased from Korean Cell Line Bank, sub-cultured three times in DMEM (Dulbecco's Modified Eagle's Medium) under 37° C. and $CO_2$ atmosphere. $1\times10^4$ cells per well were then dispensed in 96-well plate, incubated for 24 hours. The samples were treated at concentrations of 15.6, 31.3, 62.5, 125 and 250 μg/ml. After 24 hours, the cytotoxicity was evaluated using a MTT assay method.

According to the MTT assay method, 3-(4,5-dimethylthiazol-2-yl)-2,5-diphenyltetrazolium bromide reagent was purchased from Sigma and used as MTT reagent. Each cell was treated with the MTT reagent at a concentration of 0.5 mg/ml. After further incubation for 4 hours, the resulting crystal was dissolved in dimethyl sulfoxide (Sigma) and the absorbance at 595 nm was measured. The cell survival rate was converted into percentage (%) in comparison with the normal group and shown in graph.

4) Phagocytosis Assay in Macrophage $0.5\times10^4$ RAW 264.7 cells (mouse macrophage) per well were dispensed in 96 well plates and incubated for 24 hours. Each well was then treated with LPS 1 μg/ml and IgP attached with fluorescent bead. The samples were treated at concentrations of 10, 50, 100 and 200 μg/ml. After 24 hours, the culture medium of each well was removed and washed with 40 μg/ml of Trypan Blue solution. The phagocytosis in the washed plate was measured at the fluorescence wavelength of the excitation at 485 nm and the emission at 535 nm. The phagocytosis was converted into percentage (%) in comparison with the normal group. The result was shown in graph.

5) Influence on Nitrite Secretion of Macrophage $1\times10^4$ RAW 264.7 cells (mouse macrophage) per well were dispensed in 96 well plates and incubate 4 d for 24 hours. Each well was then treated with 1 μg/ml of LPS. The samples were treated at concentrations of 0, 10, 50, 100 and 200 μg/ml. After 4 hours, the culture medium of each well was taken in 100 μl to which griess reagent was added and further reacted for 15 minutes. The absorbance at 540 nm was then measured and the nitrite scavenging activity (%) was calculated.

6) Influence on Histamine Secretion of Sample

In order to confirm the influence on the histamine secretion of sample, the histamine secretion level was measured using HMC cell, a human mast cell.

$1\times10^5$ HMC cells were dispensed in 24 well plates, respectively, and then stabilized for 3 hours. The samples were treated in concentrations of 0.8, 4, 20, 100 and 200 mg/ml in each well and incubated. After 30 minutes, 1 mg/ml of compound 48/80 was treated. After 15 minutes, the medium was harvested in each well. To 100 μl of the medium, 50 μl of 1M NaOH was added and then 1 mg/ml of o-phthaldialdehyde 100 μl was added. After 4 minutes, the fluorescence at excitation 360/40 and emission 460/40 was measured and then compared with the standard solution.

7) Cytotoxicity Assay of Samples in Bronchial Epithelian Cells

The cytotoxicity of samples against bronchial epithelian cells was confirmed using A549 cell as a human bronchial epithelian cell.

The cells were purchased from Korean Cell Line Bank, sub-cultured three times in DMEM (Dulbecco's Modified Eagle's Medium) under 37° C. and 5% $CO_2$ atmosphere. $1\times10^4$ cells per well were then dispensed in 96-well plates and incubated for 24 hours. The samples were treated at concentrations of 10, 50, 100 and 200 μg/ml. After 24 hours, the cytotoxicity was evaluated using a MTT assay method.

According to the MTT assay method, 3-(4,5-dimethylthiazol-2-yl)-2,5-diphenyltetrazolium bromide reagent was purchased from Sigma and used as a MTT reagent. The MTT reagent was treated at concentration of 0.5 mg/ml in each cell. After further incubation for 4 hours, the resulting crystal was dissolved in dimethyl sulfoxide (Sigma) and the absorbance at 595 nm was measured. The cell survival rate was converted into percentage (%) as compared with the normal group and shown in graph.

8) Influence on the Inflammation Related Cytokine Secretion of Samples in Bronchial Epithelian Cells In order to confirm the influence on the secretion of inflammation related cytokines, A549 cells were used as a human bronchial epithelian cells. $1\times10^5$ cells per well were dispensed in 24-well plates and incubated for 24 hours. The samples were treated at concentrations of 50 and 200 μg/ml. The inflammatory response was induced using LPS.

After incubation for 24 hours, the medium was taken and the cytokine secretion level was measured using RayBio human cytokine antibody array kit. The medium was added to the blocked membrane using a blocking buffer for 2 hours and then reacted for 2 hours. Subsequently, they were washed five times with buffers 1 and 2 for 5 minutes and then reacted with a first antibody combined with 1 ml of biotin for 3 hours. After further washings were conducted five times for five minutes, streptavidin diluents combined with HRP were added and reacted for 2 hours. After 2 hours, the membrane was washed and then reacted with an ECL buffer to quantify using a chemiluminescene imaging apparatus.

9) Statistical Analysis

The experiment result was represented as mean±SEM. The statistical analysis was conducted using one-way ANOVA. When the confidence interval (P value) was no more than 0.05, it was judged to have significance.

CONCLUSION

1) DPPH Free Radical Scavenging Activity

Figure 8:
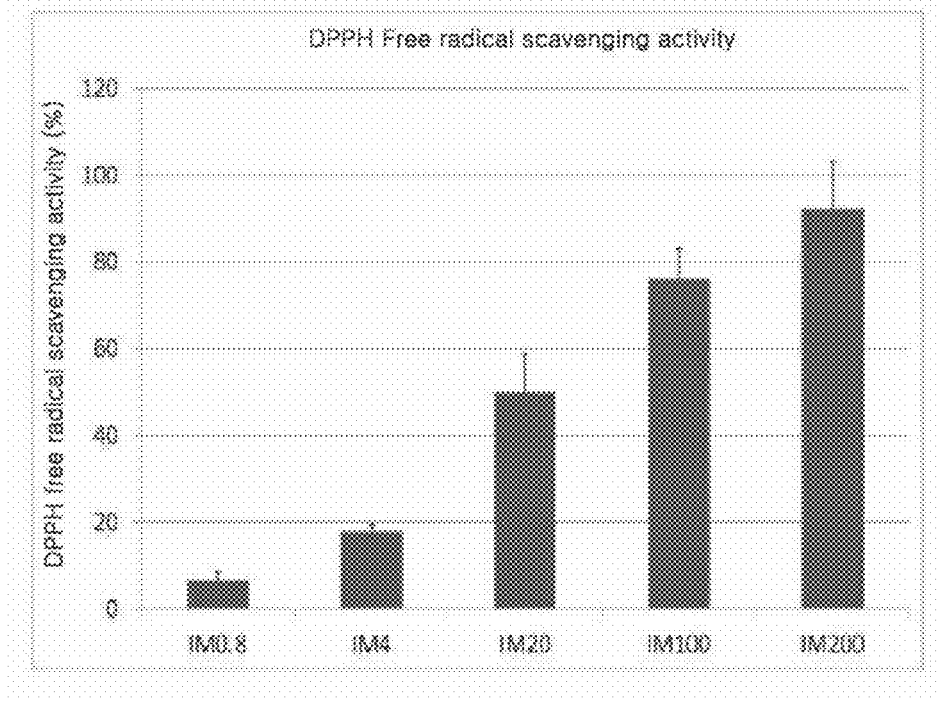
FIG. 8 is a graph representing the measurement results of DPPH free radical scavenging activity of sample (pill of Example 1) (IMO.8: sample 0.8 mg/ml treated group, IM4: sample 4 mg/ml treated group, IM20: sample 20 mg/ml treated group, IM100: sample 100 mg/ml treated group, and IM200: sample 200 mg/ml treated group).

Each sample was prepared as a test solution according to concentrations to which DPPH was added. The free radical scavenging activity was measured. As a result, the free radical scavenging activities were shown to be 6.7±2.0%, 17.9±1.6%, 49.9±8.7%, 76.1±6.9% and 92.3±11.0% at concentrations of 0.8 mg/ml, 4 mg/ml, 20 mg/ml, 100 mg/ml and 200 mg/ml, respectively, as can be confirmed in FIG. 8. It could be confirmed that as the concentrations of the samples are increased, the DPPH free radical scavenging activity is increased.

2) No Analysis

In order to confirm the effect of inhibiting the nitrite production of samples, the samples were used at concentrations of 0.8, 4, 20, 100 and 200 mg/ml to measure the nitrite scavenging activities in pH 1.2 hydrochloric acid solution, pH 3.0 of citric acid buffer and pH 6.0 of citric acid buffer.

Figure 9:
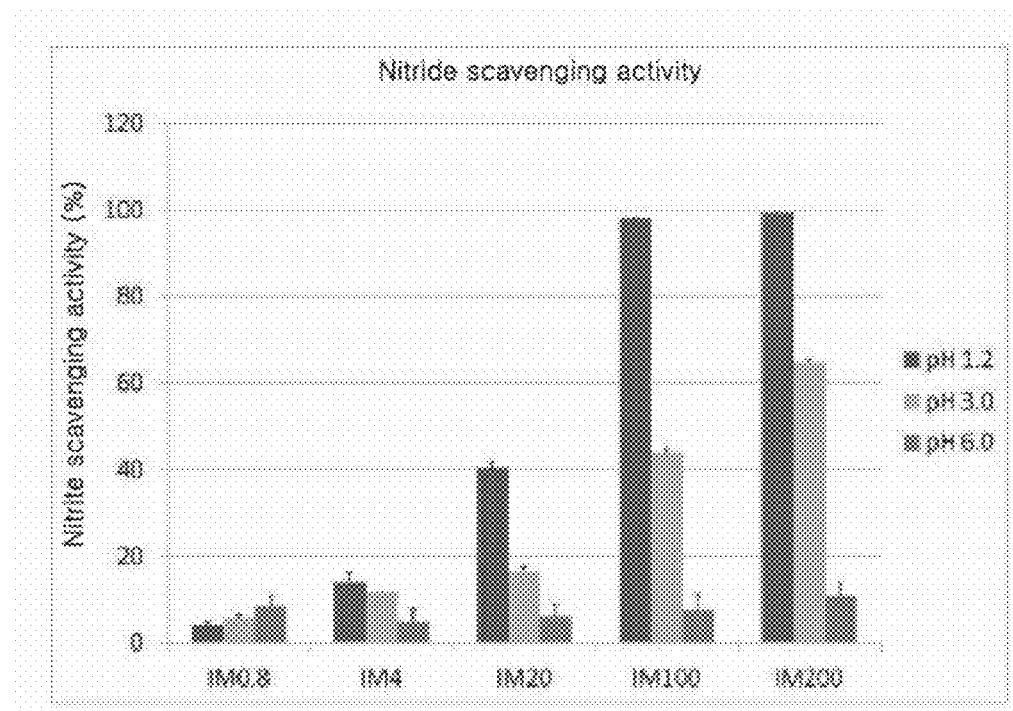
FIG. 9 is a graph representing the inhibitory effect of nitrogen oxide production of sample (pill of Example 1) (IMO.8: sample 0.8 mg/ml treated group, IM4: sample 4 mg/ml treated group, IM20: sample 20 mg/ml treated group, IM100: sample 100 mg/ml treated group, and IM200: sample 200 mg/ml treated group).

As can be confirmed in FIG. 9, the activities of inhibiting NO production in pH 1.2 of hydrochloric acid solution were 4.0±0.7%, 14.1±2.2%, 40.6±1.0%, 97.9±0.2% and 99.2±0.2%, respectively. The activity of inhibiting NO production in pH 3.0 of citric acid buffer were 5.8±0.7%, 11.6±0.2%, 16.5±0.7%, 44.1±0.7% and 64.7±0.7%, respectively. The activity of inhibiting NO production in pH 6.0 of citric acid buffer were 8.5±2.4%, 4.9±3.0%, 6.1±2.7%, 7.4±3.6% and 10.8±3.1%, respectively. Further, it can be confirmed that the activity of inhibiting NO production under pH 1.2 and pH 3.0 atmospheres were increased according to the dose of administration and that samples 100 mg/ml and 200 mg/ml treated groups under a pH 1.2 atmosphere inhibited substantially most of the NO production.

3) Cytotoxicity Assay of Sample in Macrophage

The samples were treated in RAW 264.7 cell as a mouse macrophage, to confirm the cytotoxicity of sample against the immune cell.

Figure 10:
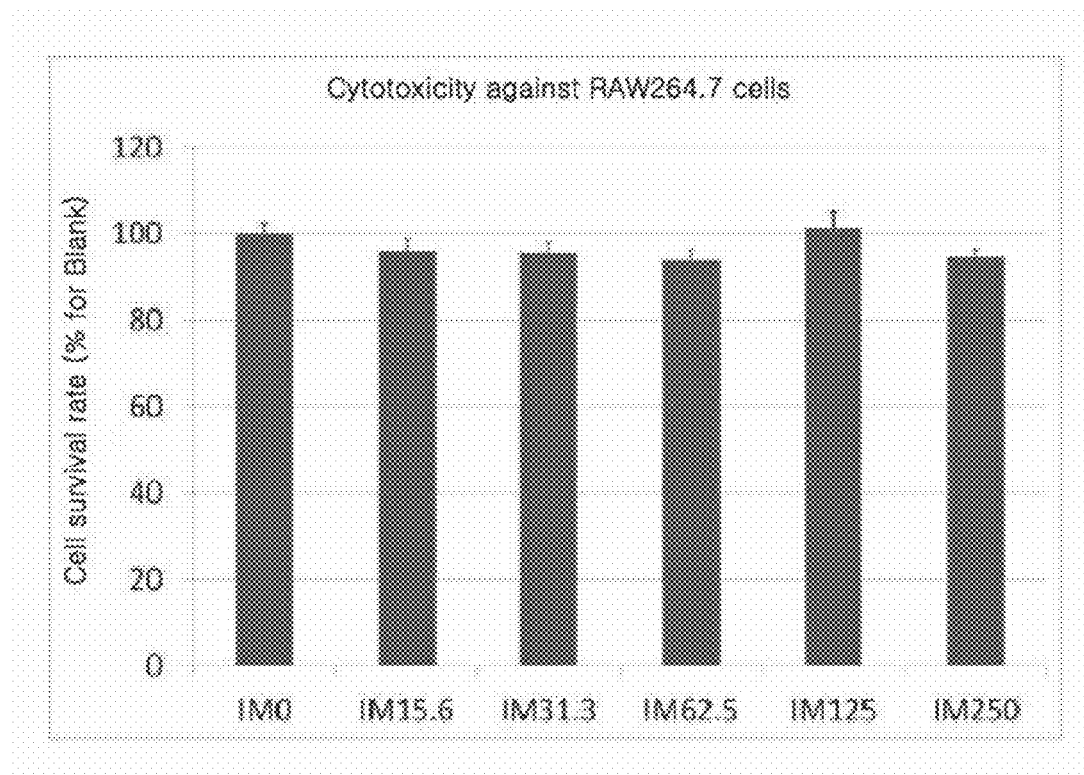
FIG. 10 is a graph identifying the cytotoxicity of sample (pill of Example 1) in macrophage (IMO: untreated group, IM15.6: sample 15.6 µg/ml treated group, IM31.3: sample 31.3 µg/ml treated group, IM62.5: sample 62.5 µg/ml treated group, IM125: sample 125 µg/ml treated group and IM250: sample 250 µg/ml treated group).

As can be seen in FIG. 10, the untreated group (IMO) exhibited the cell survival rates of 100±2.5%. The groups administered with 15.6 µg/ml, 31.3 µg/ml, 62.5 µg/ml, 125 µg/ml and 250 µg/ml of samples exhibited the cytotoxicity of 95.9±3.0%, 95.6±2.5%, 94.0±2.2%, 101.4±3.7% and 94.8±1.5%, respectively. As the result of the experiment, a statistically significant cytotoxicity in the entire administration interval could not be confirmed.

4) Phagocytosis Assay in Macrophage

RAW 264.7 cells (mouse macrophage) were treated with IgG attached with a fluorescent bead. The samples were treated according to concentrations to measure the influence on macrophage activity of samples.

Figure 11:
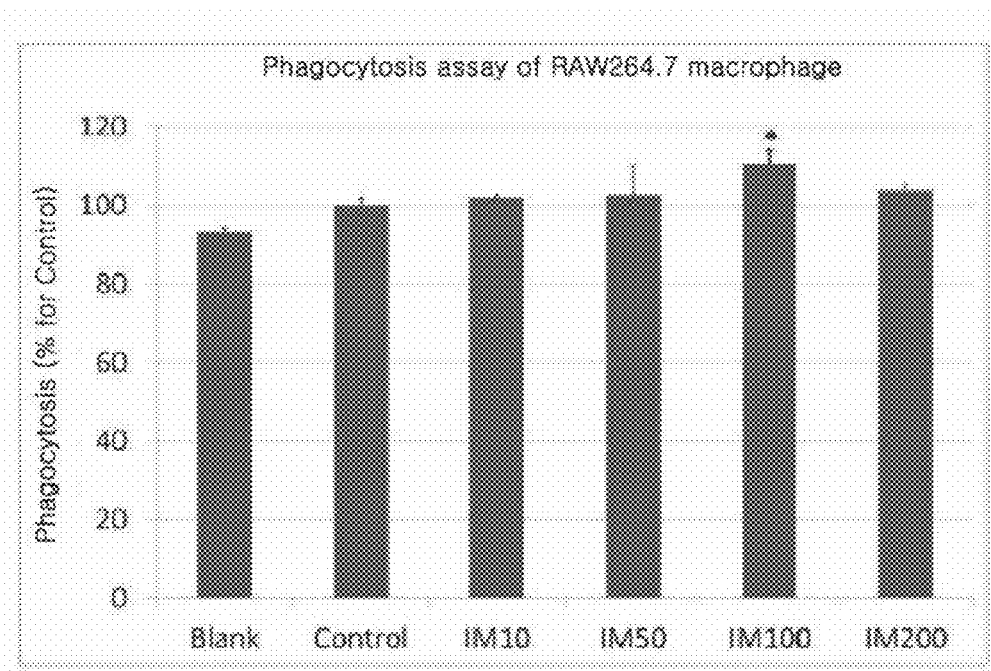
FIG. 11 is a graph showing the influence on the phagocytosis of sample (pill of Example 1) in macrophage (Blank: untreated group, Control: LPS treated group, IM10: LPS+sample 10 µg/ml treated group, IM50: LPS+sample 50 µg/ml treated group, IM100: LPS+sample 100 µg/ml treated group and IM200: LPS+sample 200 µg/ml treated group).

As can be seen from FIGS. 11 and 12, LPS treated group (control) exhibited the phagocytosis of 100.0±1.9%. The untreated group (blank) exhibited the phagocytosis of 93.3±1.1%. The groups administered with 10 µg/ml, 50 µg/ml, 100 µg/ml and 200 µg/ml of samples exhibited the phagocytosis of 102.7±0.7%, 102.7±7.3%, 110.5±3.7% and 103.8±1.8%, respectively.

It has been shown that the phagocytosis of macrophage was increased in a little by the treatment of samples. The group (IM100) administered with 100 µg/ml of sample exhibited a statistically significant phagocytosis (*p<0.05).

5) Influence on Nitrite Secretion of Macrophage

RAW 264.7 cells (mouse macrophage) were treated with LPS. The samples were treated according to concentrations to measure the influence of samples on NO production.

Figure 13:
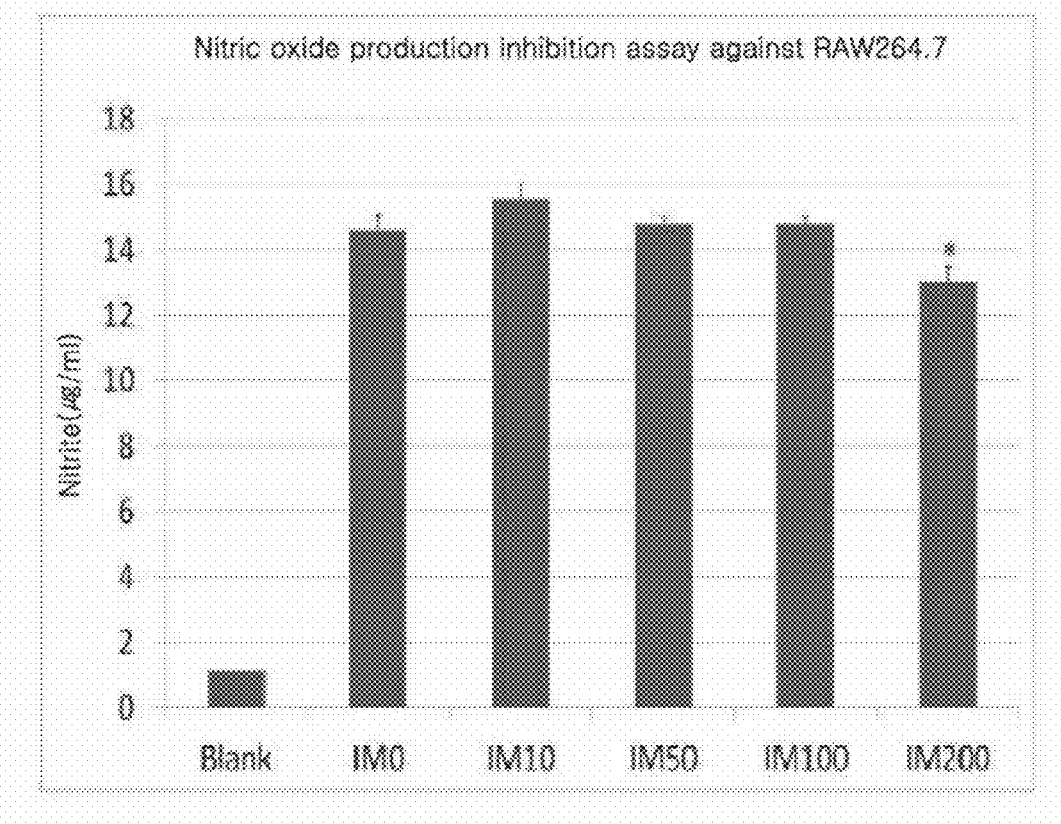
FIG. 13 is a graph confirming the inhibitory effect of nitrogen oxide production of sample (pill of Example 1) (Blank: untreated group, IMO: LPS treated group, IM10: LPS+sample 10 µg/ml treated group, IM50: LPS+sample 50 µg/ml treated group, IM100: LPS+sample 100 µg/ml treated group and IM200: LPS+sample 200 µg/ml treated group).

As can be seen from FIG. 13, the untreated group (blank) produced 1.2±0.0 µg/ml of NO. After stimulation with LPS, the groups administered with 0 µg/ml, 10 µg/ml, 50 µg/ml, 100 µg/ml and 200 µg/ml of samples produced 14.6±0.4 µg/ml, 15.6±0.4 µg/ml, 14.8±0.2 µg/ml, 14.8±0.2 µg/ml and 13.0±0.4 µg/ml of NO, respectively. As a result of the experiment, the group administered with 200 µg/ml of sample exhibited a statistically significant activity of inhibiting NO production (*p<0.05).

6) Influence on Histamine Secretion

In order to confirm the influence of samples on the histamine secretion, the histamine secretion level was measured using HMC cell as a human mast cell.

Figure 14:
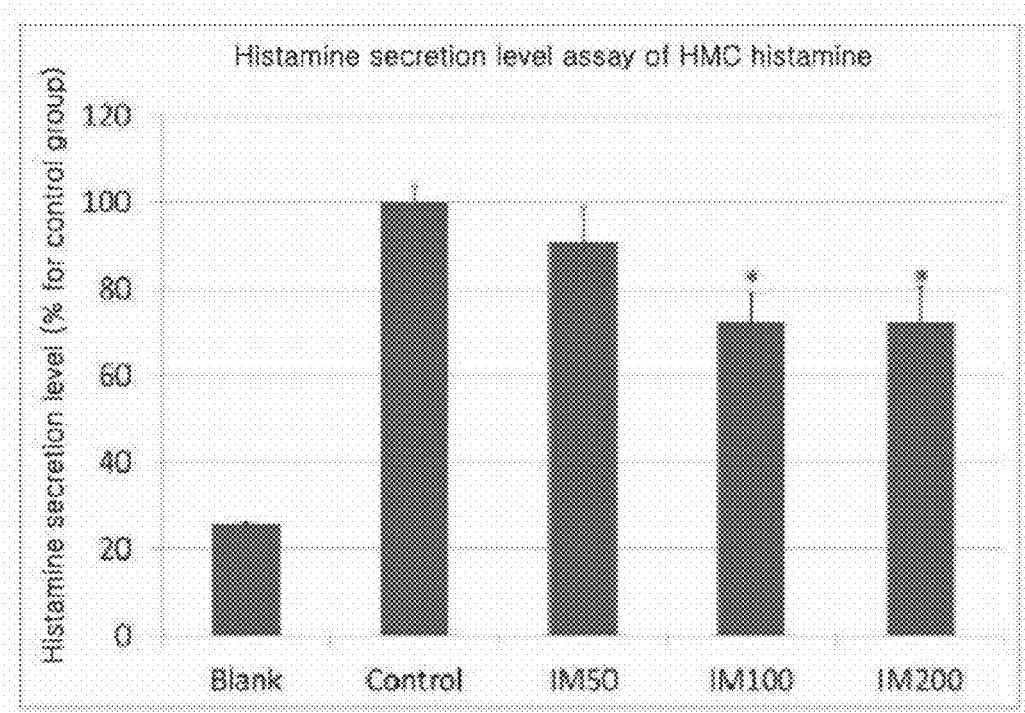
FIG. 14 is a graph which confirms the effect of histamine secretion of the composition according to the present invention (Blank: untreated group, Control: compound 48/80 treated group, IM50: compound 48/80+sample 50 µg/ml treated group, IM100: compound 48/80+sample 100 µg/ml treated group, and IM200: compound 48/80+sample 200 µg/ml treated group).

As can be seed from FIG. 14, the experiment group (control) stimulated with compound 48/80 exhibited 100±3.8% of the histamine secretion level. The untreated group (blank) exhibited 25.7±0.4% of the histamine secretion level. The groups administered with 50 µg/ml, 100 µg/ml and 200 µg/ml of samples exhibited 90.9±8.0%, 72.4±6.9% and 72.2±8.3% of the histamine secretion level, respectively. As a result of the experiment, the group administered with 100 µg/ml and 200 µg/ml of samples exhibited a statistically significant reduction in histamine secretion level (*p<0.05).

7) Cytotoxicity Assay of Samples in Bronchial Epithelian Cells

The samples were treated with A549 cells, i.e., human bronchial epithelian cells. The cytotoxicity of samples against bronchial epithelian cells was confirmed.

Figure 15:
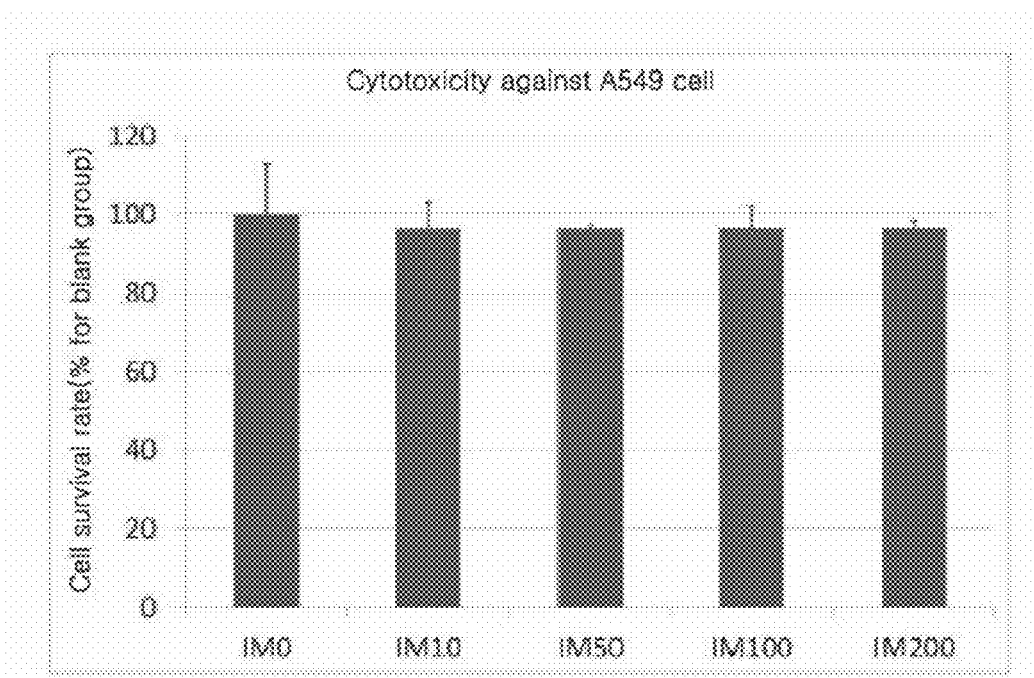
FIG. 15 is a graph representing the measurement results of the cytotoxicity to bronchial epithelian cells of sample (pill of Example 1) (IMO: untreated group, IM10: sample 10 mg/ml treated group, IM50: sample 50 mg/ml treated group, IM100: sample 100 mg/ml treated group, and IM200: sample 200 mg/ml treated group).

As can be seen from FIG. 15, the untreated group (IMO) exhibited 100.0±12.7% of cell survival rate. The groups administered with 10 µg/ml, 50 µg/ml, 100 µg/ml and 200 µg/ml of samples exhibited 96.4±6.7 µg/ml 96.4±0.8 µg/ml 96.7±5.5% and 96.6±1.9% of cell survival rate, respectively. As a result of the experiment, a statistically significant cytotoxicity in the entire administration interval could not be confirmed.

8) Influence on the Inflammation Related Cytokine Secretion of Samples in Bronchial Epithelian Cells In order to confirm the influence on the inflammation related cytokine secretion of samples, the samples were introduced in concentrations of 50 µg/ml and 200 µg/ml in A549 cells stimulated using LPS. The cytokine secretion level was then measured using RayBio human cytokine antibody array kit.

Figures 16A, 16B, 16C, 16D:
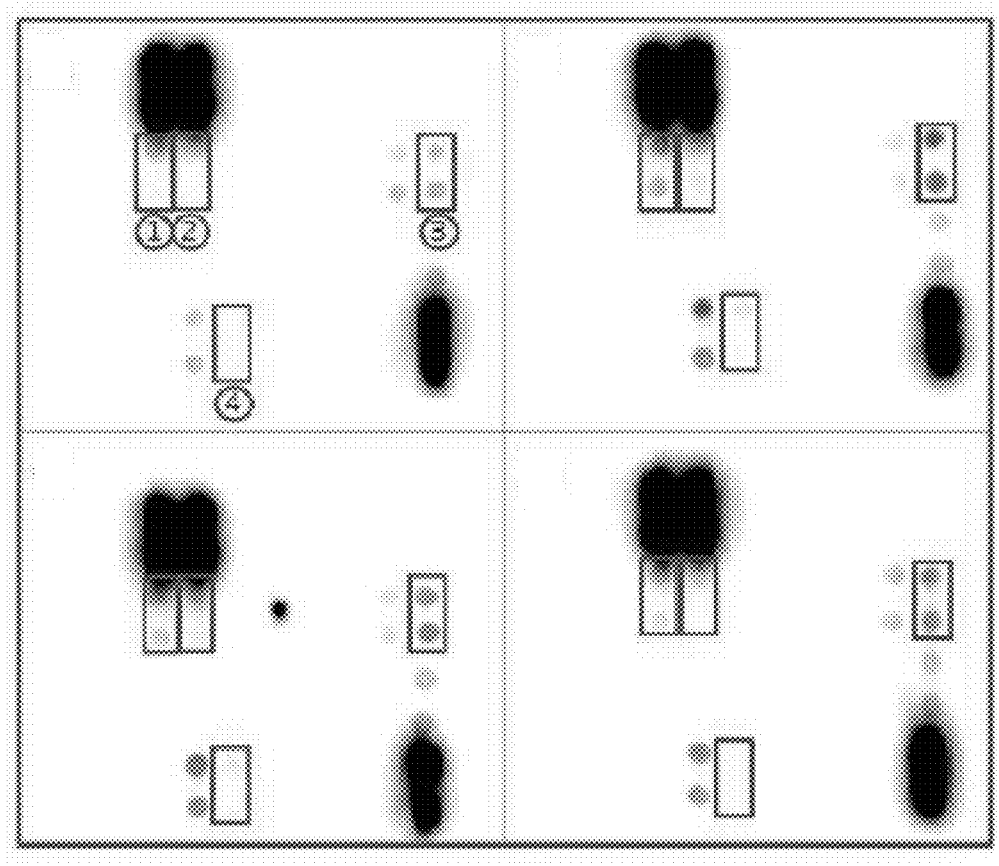
FIGS. 16A-D confirm the influence on cytokine secretion of the pill of Example 1 using RayBiop human cytokine antibody assay kit (A: untreated group, B: LPS treated group, C: LPS+sample 50 µg/ml treated group and D: LPS+sample 200 µg/ml treated group, ①: IL-1α, ②: IL-2, ③: IL-10, ④: TNF-β).

As a result, as shown in FIG. 16, the group (D) administered with 200 µg/ml of sample exhibited an inhibition in the secretion of IL-1α, IL-2, IL-10 and TNF-β.

Although the present invention has been disclosed with reference to specific examples, those skilled in the art will appreciate that various modifications, additions and substitutions are possible, without departing from the scope and spirit of the invention as disclosed in the accompanying claims.

The invention claimed is:

1. A composition for treating immune related diseases comprising *Eugenia caryophyllate*, Scorpion, Cinnabar, *Bos taurus domesticus* Gmelin, *Bombyx* Batryticatus., *Aconitum koreanum* R. Raymund, Alunitum Siccus., *Hominis* Placenta, Borneolum syntheticum and arsenic compounds.

2. The composition of claim 1 wherein the immune related diseases are selected from the group consisting of immune mediated inflammation diseases, nonimmune mediated inflammation diseases, infectious diseases, immune deficiency diseases, and neoplasia.

3. The composition of claim 2 wherein the immune related diseases are an acquired immune deficiency syndrome (AIDS), a hepatitis, a liver cirrhosis, a cancer, an asthma, an allergic rhinitis, an atopic dermatitis, a food hypersensitivity and a hives.

4. A composition for treating oxidative stress related diseases comprising *Eugenia caryophyllate*, Scorpion, Cinnabar, *Bos taurus domesticus* Gmelin, *Bombyx* Batryticatus, *Aconitum koreanum* R. Raymund, Alunitum Siccus., *Hominis* Placenta, Borneolum syntheticum and arsenic compounds.

5. The composition of claim 4 wherein the oxidative stress related diseases are a lipid metabolism disease, a vascular sclerosis, a heart failure, a hypertensive heart failure, an arrhythmia, a myocardial infraction, an angina pectoris, an ageing, an immune diseases and a cancer.

6. The composition of claim 1 wherein the arsenic compounds are selected from the group consisting of arsenic trioxide ($As_2O_3$), arsenic hexoxide ($As_4O_6$), arsenic tribromide ($AsBr_3$), arsenic trichloride ($AsCl_3$), arsenic triiodide ($AsI_3$) and melarsoprol.

7. The composition of claim 1 wherein the composition comprises 1 through 7 parts by weight of arsenic compounds, 15 through 25 parts by weight of *caryophyllate*, 200 through 270 parts by weight of Scorpion, 20 through 30 parts by weight of Cinnabar, 25 through 35 parts by weight of *Bos taurus domesticus* Gmelin, 50 through 65 parts by weight of *Bombyx* Batryticatus, 38 through 48 parts by weight of *Aconitum koreanum* R. Raymund, 50 through 65 parts by weight of Alunitum Siccus., 200 through 270 parts by weight of *Hominis* Placenta, and 0.5 through 6 parts by weight of Borneolum syntheticum.

8. The composition of claim 1 wherein the composition comprises 3 through 5 parts by weight of arsenic compounds, 17 through 22 parts by weight of *caryophyllate*, 220 through 250 parts by weight of Scorpion, 22 through 27 parts by weight of Cinnabar, through 31 parts by weight of *Bos taurus domesticus* Gmelin, 55 through 62 parts by weight of *Bombyx* Batryticatus, 41 through 46 parts by weight of *Aconitum koreanum* R. Raymund, 55 through 62 parts by weight of Alunitum Siccus., 220 through 250 parts by weight of *Hominis* Placenta, and 2 through 4 parts by weight of Borneolum syntheticum.

9. An antioxidant composition comprising *Eugenia caryophyllate*, Scorpion, Cinnabar, *Bos taurus domesticus* Gmelin, *Bombyx* Batryticatus, *Aconitum koreanum* R. Raymund, Alunitum Siccus., *Hominis* Placenta, Borneolum syntheticum and arsenic compounds.

10. A composition for the reduction in toxicity of arsenic compounds comprising *Eugenia caryophyllate*, Scorpion, Cinnabar, *Bos taurus domesticus* Gmelin, *Bombyx* Batryticatus, *Aconitum koreanum* R. Raymund, Alunitum Siccus., *Hominis* Placenta, Borneolum syntheticum and arsenic compounds.

11. The composition of claim 4 wherein the arsenic compounds are selected from the group consisting of arsenic trioxide ($As_2O_3$), arsenic hexoxide ($As_4O_6$), arsenic tribromide ($AsBr_3$), arsenic trichloride ($AsCl_3$), arsenic triiodide ($AsI_3$) and melarsoprol.

12. The composition of claim 4 wherein the composition comprises 1 through 7 parts by weight of arsenic compounds, 15 through 25 parts by weight of *caryophyllate*, 200 through 270 parts by weight of Scorpion, 20 through 30 parts by weight of Cinnabar, 25 through 35 parts by weight of *Bos taurus domesticus* Gmelin, 50 through 65 parts by weight of *Bombyx* Batryticatus, 38 through 48 parts by weight of *Aconitum koreanum* R. Raymund, 50 through 65 parts by weight of Alunitum Siccus., 200 through 270 parts by weight of *Hominis* Placenta, and 0.5 through 6 parts by weight of Borneolum syntheticum.

13. The composition of claim 4 wherein the composition comprises 3 through 5 parts by weight of arsenic compounds, 17 through 22 parts by weight of *caryophyllate*, 220 through 250 parts by weight of Scorpion, 22 through 27 parts by weight of Cinnabar, 27 through 31 parts by weight of *Bos taurus domesticus* Gmelin, 55 through 62 parts by weight of *Bombyx* Batryticatus, 41 through 46 parts by weight of *Aconitum koreanum* R. Raymund, 55 through 62 parts by weight of Alunitum Siccus., 220 through 250 parts by weight of *Hominis* Placenta, and 2 through 4 parts by weight of Borneolum syntheticum.

* * * * *